US011964244B2

(12) United States Patent
Davies et al.

(10) Patent No.: US 11,964,244 B2
(45) Date of Patent: Apr. 23, 2024

(54) METHODS OF RELEASING AND ANALYZING CELLULAR COMPONENTS

(71) Applicant: STOKES BIO LIMITED, Limerick (IE)

(72) Inventors: Mark Davies, Limerick (IE); Tara Dalton, Limerick (IE)

(73) Assignee: STOKES BIO LIMITED, Limerick (IE)

(*) Notice: Subject to any disclaimer, the term of this patent is extended or adjusted under 35 U.S.C. 154(b) by 245 days.

(21) Appl. No.: 17/197,177

(22) Filed: Mar. 10, 2021

(65) Prior Publication Data

US 2021/0299619 A1  Sep. 30, 2021

Related U.S. Application Data

(60) Continuation of application No. 16/155,411, filed on Oct. 9, 2018, now Pat. No. 10,967,338, which is a continuation of application No. 15/463,472, filed on Mar. 20, 2017, now abandoned, which is a division of application No. 12/732,769, filed on Mar. 26, 2010, now Pat. No. 9,597,644, which is a continuation-in-part of application No. 12/683,882, filed on Jan. 7, 2010, now Pat. No. 8,968,659, which is a continuation-in-part of application No. 12/617,286, filed on Nov. 12, 2009, now abandoned.

(51) Int. Cl.
| | | |
|---|---|---|
| *B01L 3/00* | (2006.01) | |
| *B01F 25/10* | (2022.01) | |
| *B01F 33/30* | (2022.01) | |
| *B01F 33/302* | (2022.01) | |
| *B01L 7/00* | (2006.01) | |
| *G01N 33/50* | (2006.01) | |
| *G01N 35/08* | (2006.01) | |
| *G01N 35/00* | (2006.01) | |
| *G01N 35/10* | (2006.01) | |

(52) U.S. Cl.
CPC ............ *B01F 25/10* (2022.01); *B01F 33/30* (2022.01); *B01F 33/3021* (2022.01); *B01L 3/502784* (2013.01); *B01L 7/525* (2013.01); *G01N 33/5008* (2013.01); *G01N 35/08* (2013.01); *B01L 2200/0636* (2013.01); *B01L 2200/0673* (2013.01); *B01L 2300/0816* (2013.01); *B01L 2300/0861* (2013.01); *B01L 2300/087* (2013.01); *B01L 2300/185* (2013.01); *B01L 2400/0409* (2013.01); *B01L 2400/0487* (2013.01); *G01N 2035/00514* (2013.01); *G01N 35/1095* (2013.01)

(58) Field of Classification Search
CPC ............ B01L 3/502784; B01L 7/525; B01L 2200/0673; B01L 2300/0816; B01L 2300/0861; B01L 2300/087; B01L 2400/0409; B01L 2400/0487; G01N 33/5008

USPC ........................................................ 435/29
See application file for complete search history.

(56) References Cited

U.S. PATENT DOCUMENTS

| | | |
|---|---|---|
| 4,766,082 A | 8/1988 | Marteau D'Autry |
| 5,102,517 A | 4/1992 | Fuchs et al. |
| 5,270,183 A | 12/1993 | Corbett et al. |
| 5,720,923 A | 2/1998 | Haff et al. |
| 5,779,977 A | 7/1998 | Haff et al. |
| 5,827,480 A | 10/1998 | Haff et al. |
| 6,033,880 A | 3/2000 | Haff et al. |
| 6,143,496 A | 11/2000 | Brown et al. |
| 6,193,471 B1 | 2/2001 | Paul |
| 6,294,063 B1 | 9/2001 | Becker et al. |
| 6,306,590 B1 | 10/2001 | Mehta et al. |
| 6,355,164 B1 | 3/2002 | Wendell et al. |
| 6,557,427 B2 | 5/2003 | Weigl et al. |
| 6,670,153 B2 | 12/2003 | Stern |
| 6,907,895 B2 | 6/2005 | Johnson et al. |
| 7,041,181 B2 | 5/2006 | Anderson |
| 7,041,481 B2 | 5/2006 | Anderson et al. |
| 7,077,152 B2 | 7/2006 | Karp |
| 7,129,091 B2 | 10/2006 | Ismagilov et al. |

(Continued)

FOREIGN PATENT DOCUMENTS

| | | |
|---|---|---|
| DE | 99/41015 | 8/1999 |
| DE | 100 55 318 A1 | 12/2001 |

(Continued)

OTHER PUBLICATIONS

Extended Search Report (EP Form 1703) from EP Appl. No. 15 187 064.9, dated Dec. 4, 1 2015.

(Continued)

*Primary Examiner* — Christine T Mui
(74) *Attorney, Agent, or Firm* — JONES ROBB, PLLC

(57) ABSTRACT

A system for analyzing a biological sample may include at least one sample acquisition stage comprising a sample acquisition device for acquiring the biological sample from a sample source; a droplet generator device for forming a droplet wrapped in an immiscible carrier fluid, wherein the wrapped droplet comprises at least the biological sample and a reagent, the droplet generator configured to receive the biological sample transferred from the sample acquisition device; a collection vessel for collecting the wrapped sample droplet from the droplet generator, the vessel configured to contain a carrier fluid for receiving and protecting the sample droplet; and an analysis system for analyzing the wrapped sample droplet and detecting products of a polymerase chain reaction.

12 Claims, No Drawings

(56) References Cited

U.S. PATENT DOCUMENTS

| | | |
|---|---|---|
| 7,189,580 B2 | 3/2007 | Beebe et al. |
| 7,235,405 B2 | 6/2007 | Charles et al. |
| 7,238,268 B2 | 7/2007 | Ramsey et al. |
| 7,294,503 B2 | 11/2007 | Quake et al. |
| 7,459,315 B2 | 12/2008 | Brown |
| 7,622,076 B2 | 11/2009 | Davies et al. |
| RE41,780 E | 9/2010 | Anderson et al. |
| 7,955,864 B2 | 6/2011 | Cox et al. |
| RE43,365 E | 5/2012 | Anderson et al. |
| 8,298,833 B2 | 10/2012 | Davies et al. |
| 8,304,193 B2 | 11/2012 | Ismagilov et al. |
| 8,329,407 B2 | 12/2012 | Ismagilov et al. |
| 8,361,807 B2 | 1/2013 | Wiyatno et al. |
| 8,592,221 B2 | 11/2013 | Fraden et al. |
| 8,697,011 B2 | 4/2014 | McGuire et al. |
| 8,822,148 B2 | 9/2014 | Ismagilov et al. |
| 8,889,083 B2 | 11/2014 | Smagilov et al. |
| 8,968,659 B2 | 3/2015 | Davies et al. |
| 9,127,310 B2 | 9/2015 | Larson et al. |
| 9,140,630 B2 | 9/2015 | Wiyatno et al. |
| 9,322,511 B2 | 4/2016 | Davies et al. |
| 9,441,266 B2 | 9/2016 | Larson et al. |
| 9,597,644 B2 | 3/2017 | Davies et al. |
| 10,286,396 B2 | 5/2019 | Fraden et al. |
| 10,450,604 B2 | 10/2019 | Wiyatno et al. |
| 10,676,786 B2 | 6/2020 | Davies et al. |
| 10,730,051 B2 | 8/2020 | Davies et al. |
| 10,967,338 B2 | 4/2021 | Davies et al. |
| 2001/0009757 A1 | 7/2001 | Bischof et al. |
| 2001/0048637 A1 | 12/2001 | Weigl et al. |
| 2002/0060156 A1 | 5/2002 | Mathies et al. |
| 2002/0166582 A1 | 11/2002 | O'Connor et al. |
| 2003/0073089 A1 | 4/2003 | Mauze et al. |
| 2003/0138819 A1 | 7/2003 | Gong et al. |
| 2003/0170698 A1 | 9/2003 | Gascoyne et al. |
| 2004/0022686 A1 | 2/2004 | Charles et al. |
| 2004/0171055 A1 | 9/2004 | Brown |
| 2004/0180346 A1 | 9/2004 | Anderson et al. |
| 2004/0211659 A1 | 10/2004 | Velev |
| 2005/0048581 A1 | 3/2005 | Chiu et al. |
| 2005/0202489 A1 | 9/2005 | Cho et al. |
| 2005/0221339 A1 | 10/2005 | Griffiths et al. |
| 2005/0272159 A1 | 12/2005 | Ismagilov et al. |
| 2006/0205062 A1 | 9/2006 | Davies et al. |
| 2007/0014695 A1 | 1/2007 | Yue et al. |
| 2007/0039866 A1 | 2/2007 | Schroeder et al. |
| 2007/0062583 A1 | 3/2007 | Cox et al. |
| 2007/0068573 A1 | 3/2007 | Cox et al. |
| 2007/0117212 A1 | 5/2007 | Kautz et al. |
| 2007/0134209 A1 | 6/2007 | Oakey |
| 2007/0141593 A1 | 6/2007 | Lee et al. |
| 2008/0014589 A1* | 1/2008 | Link ............... C12Q 1/6806 137/896 |
| 2008/0166793 A1* | 7/2008 | Beer ............... C12Q 1/04 435/287.2 |
| 2008/0277494 A1 | 11/2008 | Davies et al. |
| 2010/0022414 A1 | 1/2010 | Link et al. |
| 2010/0041086 A1 | 2/2010 | Pamula et al. |
| 2010/0059120 A1 | 3/2010 | Tian |
| 2010/0092987 A1 | 4/2010 | Davies et al. |
| 2010/0297685 A1 | 11/2010 | Davies et al. |
| 2011/0059556 A1 | 3/2011 | Strey et al. |
| 2011/0171748 A1 | 7/2011 | Cox et al. |
| 2013/0183210 A1 | 7/2013 | Wiyatno et al. |
| 2016/0097087 A1 | 4/2016 | Wiyatno et al. |
| 2016/0339435 A1 | 11/2016 | Davies et al. |
| 2017/0081705 A1 | 3/2017 | Davies et al. |

FOREIGN PATENT DOCUMENTS

| | | |
|---|---|---|
| EP | 1 508 044 B1 | 9/2010 |
| EP | a3 299 469 a1 | 3/2018 |
| FR | 2 839 504 | 11/2003 |
| WO | 01/01106 A1 | 1/2001 |
| WO | 01/89675 A2 | 11/2001 |
| WO | 02/23163 A1 | 3/2002 |
| WO | 02/40874 A1 | 5/2002 |
| WO | 02/072264 A1 | 9/2002 |
| WO | 03/016558 | 2/2003 |
| WO | 2003016558 | 2/2003 |
| WO | 03/057010 A2 | 7/2003 |
| WO | 2004038363 A2 | 12/2004 |
| WO | 2005002730 | 1/2005 |
| WO | 2005023427 | 3/2005 |
| WO | 2005059512 | 9/2005 |
| WO | 2005080606 A1 | 9/2005 |
| WO | 2007091228 | 8/2007 |
| WO | 2007091229 | 8/2007 |
| WO | 2007091230 | 8/2007 |
| WO | 2007133710 | 11/2007 |
| WO | 2008038259 | 4/2008 |

OTHER PUBLICATIONS

Nakano, H. et al., "High Speed Polymerase Chain Reaction in Constant Flow", Biosci. Biotech. Biochem, vol. 58 (2), Jun. 12, 2014, 349-352.

Brouzes, Eric et al., "Droplet Microfluidic Technology for Single-Cell High-throughput Screening", Proceedings of the National Academy of Sciences, vol. 106, No. 34, 2009, 14195-14200.

Medkova, Martina et al., "Analyzing Cancer at Single Cell Resolution with Droplet Technology", American Association of Cancer Research, RainDance Technologies, Apr. 19, 2010.

04770390.5, Office Action dated Apr. 28, 2011, 3 pgs.

U.S. Appl. No. 12/617,286, Office Action dated May 23, 2011, 10 pgs.

U.S. Appl. No. 12/683,882, Office Action dated Nov. 24, 2010, 16 pgs.

U.S. Appl. No. 12/617,286, Office Action dated Oct. 15, 2010, 7 pgs.

Bernard, "Real-time PCR technology for cancer diagnostics", Clinical Chemistry 48(8) 2002, 1178-85.

Yang J.; Huang Y.; Wang X.-B.; Becker, F.F.; Gascoyne, R.C. "Cell Separation on Microfabricated Electrodes Using Dielectrophoretic/Gravitational Field-Flow Fractionation" Anal. Chem. 1999, 71, pp. 91-918.

Meriam-Webster.com definition of "segment", obtained on Jul. 7, 2015, pp. 1-4.

Kumaresan, P.; Yang, C.J.; Cronier, S.A.; Blazej, R.G.; Mathies, R.A.; "High-Throughput Single Copy DNA Amplification and Cell Analysis in Engineered Nanoliter Droplets", Anal. Chem., 2008, 80, pp. 3522-3529.

He, M.; Edgar, J.S.; Jeffries, G.D.M.; Lorenz, R.M.; Shelby, J.P.; Chiu, D.T. "Selective Encapsulation of Single Cells and Subcellular Organelles into Picoliter-and Femtoliter-Volume Droplets", Anal. Chem. 2005, 77, pp. 1539-1544.

Curran, K.; Colin, S.; Baldas, L. "Liquid bridge instability applied to microfluidics", Microfluid Nanfluid, 2005, pp. 336-345.

Newport, D.; Davies, M.; Dalton, T. "Microfluidics for Genetic Caner Diagnostics", La Houille Blanche, Jan.-Feb. 2006, 1, pp. 26-33.

Nakano, M.; Komatsu, J.; Matsuura, S.; Takashima, K.; Katsure, S.; Mizuno, A. "Single-Molecule PCR using water-in-oil emulstion", Journal of Biotechnology, 2003, 102, pp. 117-124.

Thouas, G.A.; Jones, G.M.; Trounson, A.O. "The 'GO' system—a novel method of microculture for in vitro development of mouse zygotes to the blastocyst strage", Reproduction, 2003, 126, pp. 161-169.

Geun Chung, B.; Flanagan, L.A.; Rhee, S.W.; Schwartz, P.H.; Monuki, E.S.; Jeon, N.L., "Human neural stem cell growth and differentiation in a gradient-generating microfludic device", Lab on a Chip, 2005, 5, pp. 401-406.

J.W. Pollard and J.M. Walker (Basic Cell Culture Protocols, 2nd ed.: Methods in Molecular Biology, vol. 75, Humana Press, 1997).

J. Davis (Basic Cell Culture: A Practical Approach, 2nd ed., Oxford University Press, 2002).

(56) References Cited

OTHER PUBLICATIONS

S. Ozturk and W. Hu (Cell Culture Technology for Pharmaceutical and Cell-Based Therapies, CRC Press, 2005).
A. Doyle and J.B. Griffiths (Cell and Tissue Culture for Medical Research, John Wiley & Sons, Ltd, 2000).
A. Doyle, J.B. Griffiths (Cell and Tissue Culture: Laboratory Procedures in Biotechnology, John Wiley & Sons, Ltd, (1998).
R. Ian Freshney (Culture of Animal Cells: A Manual of Basic Techniques, 5th ed., John Wiley & Sons, 2005).
G. Vunjak-Novakovic and R.I. Freshney (Culture of Cells for Tissue Engineering, John Wiley & Sons, 2006).
R. Pfragner and R. Freshney (Culture of Human Tumor Cells, John Wiley & Sons, 2003).
The Merck Index (14th edition. Whitehouse Station, New Jersey, 2009).
Dorr et al. (Cancer Chemotherapy Handbook, 2d edition, pp. 15-34, Appleton & Lange, Connecticut, 1994).
"Fluoromed" [online] retrieved from http://fluoromed.com/products/perfluoroperhydrophenanthrene.html., May 17, 2011.
International Preliminary Report on Patentability for PCT/US2011/030034, dated Oct. 2, 2012.

\* cited by examiner

METHODS OF RELEASING AND ANALYZING CELLULAR COMPONENTS

RELATED APPLICATIONS

This application is a continuation application U.S. patent application Ser. No. 16/155,411, filed Oct. 9, 2018, which is a continuation application of U.S. patent application Ser. No. 15/463,472, filed Mar. 20, 2017 (now abandoned), which is a divisional application of U.S. patent application Ser. No. 12/732,769, filed Mar. 26, 2010 (now U.S. Pat. No. 9,597,644), which is a continuation-in-part of U.S. patent application Ser. No. 12/683,882, filed Jan. 7, 2010 (now U.S. Pat. No. 8,968,659), which is a continuation-in-part of U.S. patent application Ser. No. 12/617,286, filed Nov. 12, 2009 (now abandoned), the contents of each of which are incorporated by reference herein in their entirety. Related applications include U.S. patent application Ser. No. 11/366,524, filed Mar. 3, 2006 (now U.S. Pat. No. 7,622,076), which is a continuation of PCT/IE2004/000115 filed Sep. 6, 2004 and published in English (now expired), which claims the priorities of U.S. patent application Ser. Nos. 60/500,344 and 60/500,345, both filed on Sep. 5, 2003. The contents of each of these applications are incorporated by reference herein in their entirety.

FIELD OF THE INVENTION

The present invention generally relates to methods for culturing and analyzing cells using liquid bridges.

BACKGROUND

A broad range of therapies exist that may be used to treat patients afflicted with diseases, such as infections, cardiovascular disease, and neoplastic disease. Use of those therapies has revealed substantial differences in therapeutic response among individual. Any given drug may be therapeutic in some individuals while being ineffective in others. Further, a drug may produce adverse effects in certain individuals whereas others do not experience the same adverse reaction to the drug. Recognition of differences in drug response among individual is an important step towards optimizing therapy.

A problem with current approaches in drug therapy is that those therapies are designed for treatment of large patient populations as groups, irrespective of the potential for individual based differences in drug response. This approach is utilized due to costs and time associated with producing numerous cultures of an individual's cells, which is required for screening many different drugs as potential agents for effective disease treatment for a particular individual. This problem is particularly acute in the field of cancer therapy, in which tumors have qualities specific to individuals and individuals respond very differently to the same chemotherapeutic agent.

There is a need for methods that can rapidly and cost effectively culture and analyze an individual's cells so that personalized treatment protocols may be developed and implemented.

SUMMARY

The present invention provides improved methods cell culturing and drug screening. In general, the invention involves using liquid bridges to produce droplets having at least one cell. Liquid bridges are used to produce sample droplets that contain reaction components for rapid analysis of small sample volumes. Liquid bridges allow the formation of sample droplets through the interaction of immiscible fluids. The droplets may be dispensed into individual vessels for culturing of the cells or mixed with drugs to analyze the affect of the drug on the cell. Use of liquid bridges provides for an automated system with high throughput for preparing cell cultures and for analyzing affect of drugs on cells. Thus the invention provides significant improvements in speed and cost associated with culturing and/or analyzing cells.

In certain aspects, methods of the invention are used for high throughput formation of droplets wrapped in an immiscible carrier fluid, in which the droplets contain at least one cell. The droplets may then be dispensed and the cells are either cultured in the droplets or the droplets are burst and the cells are cultured in the vessel to which they are dispensed. Droplets may be generated in numerous ways, although a preferred method is using liquid bridges. One method of generating a sample droplet including at least one cell involves dipping an open ended channel into the first vessel to produce a sample droplet including at least one cell. Another method of generating the sample droplet involves flowing a sample fluid including the plurality of cells to a liquid bridge, in which the liquid bridge segments the sample fluid to produce the wrapped sample droplets.

Prior to dispensing, the sample droplets may be mixed with cell culture media to produce a mixed wrapped droplet. Droplet mixing may be accomplished by flowing the sample droplets to a liquid bridge to mix with droplets of cell culture media to produce the mixed wrapped droplet. The sample droplets and the cell culture droplets may flow through a same channel, and flow may be used to cause the droplets to mix at the liquid bridge to form the mixed wrapped droplet. Alternatively, the sample droplets and the cell culture media droplets may flow through different channels and meet for mixing at the liquid bridge.

Methods of the invention involve dispensing the sample droplets to vessels for culturing. In particular embodiments, the cells are dispensed to individual wells of a well plate, e.g., 96 well or 384 well plate. Dispensing may be accomplished by generating a siphoning effect, and then using the siphoning affect to dispense the droplets. In certain embodiments, the droplets are dispensed without a substantial amount of carrier fluid.

Methods of the invention may be used to prepare any type of cell for culturing, such as mammalian cells, e.g., human cells. In certain embodiments, the cells are obtained from a human tissue or body fluid. In particular embodiments, the cells are obtained from a tumor. In other embodiments, the cells are brain cells or embryonic cells. The starting mixture of cells may be either homogeneous (i.e., a mixture including all the same type of cells) or heterogeneous (i.e., a mixture including a plurality of different types of cells).

Another aspect of the invention provides methods for analyzing the affect of at least one agent on a cell or cellular component. Those methods of the invention involve forming a droplet wrapped in an immiscible carrier fluid, in which the droplet includes at least one cell or cellular component and at least one agent, and analyzing the wrapped droplet to determine the affect of the agent on the cell or cellular component. Analyzing of the cells may occur while the wrapped droplets are flowing through a channel. Alternatively, the droplets may be dispensed to a vessel, such as individual wells of a well plate, prior to analysis. In certain embodiments, a liquid bridge is used to form the wrapped droplets. In certain embodiments, the cells are lysed prior to being analyzed.

Methods of the invention may be used to analyze affect of any agent, or combination of agents, on any cell or combination of cells. In certain embodiments, the cell is a cancerous cell and the agent is an anti-cancer agent or a combination of anti-cancer agents. In other embodiments, different concentrations of the same agent are analyzed.

DETAILED DESCRIPTION

The present invention generally relates to methods for culturing and analyzing cells using liquid bridges. Certain aspects of the invention provide methods for culturing cells. The starting mixture of cells may be either homogeneous (i.e., a mixture including all the same type of cells) or heterogeneous (i.e., a mixture including a plurality of different types of cells). Methods of the invention involve generating sample droplets wrapped in an immiscible carrier fluid including at least one cell.

Wrapped droplet generation may be accomplished by numerous techniques. The wrapped droplets may be formed, for example, by dipping an open ended tube into a vessel. Exemplary sample acquisition devices are shown in McGuire et al. (U.S. patent application Ser. No. 12/468, 367), the contents of which are incorporated by reference herein in their entirety. Parameters such as channel diameter, dipping time, and system flow, may be adjusted so that wrapped droplets are formed in which each droplet contains only a single cell.

Another method for generating wrapped droplets involves using a liquid bridge. The liquid bridge is used to segment a flow of sample fluid into individual wrapped droplets. The droplets formed in a liquid bridge are enveloped in an immiscible carrier fluid. A typical liquid bridge of the invention is formed by an inlet in communication with a chamber that is filled with a carrier fluid. The carrier fluid is immiscible with sample fluid flowing through the inlet into the chamber. The sample fluid expands until it is large enough to span a gap between the inlet and an outlet in communication with the chamber. Droplet formation is accomplished by adjusting flow rate, resulting in formation of an unstable funicular bridge that subsequently ruptures from the inlet. After rupturing from the inlet, the sample droplet enters the outlet, surrounded by the carrier fluid from the chamber. Further description of using liquid bridges for droplet formation is shown in Davies et al. (International patent publication number WO 2007/091228), the contents of which are incorporated by reference herein in their entirety. Because droplet formation is controlled by flow rate, the flow rate may be adjusted to ensure that droplets are formed in which each droplet contains only a single cell.

In certain embodiments, droplets are formed such that each droplet contains only a single cell. Poisson statistics dictate the dilution requirements needed to ensure that each wrapped droplet contains only a single cell. For example, if, on average, each wrapped droplet is to contain only a single cell, about 1/3 of the droplets will be empty and contain no cell, about 1/3 will contain exactly one cell, and about 1/3 will contain two or more cells.

The droplet population may be enriched to maximize the fraction that started with a single cell. For example, the population of cells may be fluorescently tagged and thus it is possible to flow sort the wrapped droplets after droplet formation to enrich for those that are fluorescent rather than empty. High-speed flow sorters, such as the MoFlo (Beckman-Coulter, Inc., Fullerton, California), are capable of sorting at rates in excess of 70,000 per second and can be used to enrich a population of wrapped droplets of the invention. Similarly, it is possible to exploit other differences between empty and full wrapped droplets (e.g., buoyant density) to enrich a population of droplets. In order to enrich for droplets with one cell as opposed to several cells, it may be desirable to skew the Poisson distribution accordingly.

In certain embodiments, the sample droplets may be mixed with cell culture media prior to dispensing of the droplet to produce a mixed wrapped droplet including at least one cell and culture media. Any device that is capable of mixing sample droplets to form mixed sample droplets wrapped in an immiscible carrier fluid may be used with methods of the invention. An exemplary droplet mixing device is a liquid bridge. For droplet mixing in a liquid bridge, the sample droplet containing the cell flows to an inlet and enters a chamber that is filled with a carrier fluid. The carrier fluid is immiscible with the sample droplet. The sample droplet expands until it is large enough to span a gap between inlet and outlet ports. Droplet mixing can be accomplished in many ways, for example, by adjusting flow rate or by introducing a droplet of cell culture media to the sample droplet from a second inlet, forming an unstable funicular bridge that subsequently ruptures from the inlet. After rupturing from the inlet, the mixed sample droplet enters the outlet, surrounded by the carrier fluid from the chamber. Further description of using liquid bridges for droplet mixing is shown in Davies et al. (International patent publication number WO 2007/091228).

The sample droplets and the cell culture media droplets may flow through a same channel, and flow may be used to cause the droplets to mix at the liquid bridge to form the mixed wrapped droplet. Alternatively, the sample droplets and the cell culture media droplets may flow through different channels and meet for mixing at the liquid bridge.

After droplet generation, the cells in the droplets are cultured. In certain embodiments, the wrapped droplets are dispensed to a vessel or vessels for culturing of the cells in the droplets. In particular embodiments, the vessel is a well plate, e.g. 96 well or 384 well, and the droplets are dispensed to individual wells of the well plate. Droplet dispensing may be accomplished in numerous ways. In certain embodiments, a system is configured to produce a siphoning effect. The siphoning effect refers to flow that is driven by a difference in hydrostatic pressure without any need for pumping. The effect is produced by configuring a system such that a dispensing end or port is lower than a fluid surface at an acquisition point, e.g., a sample acquisition stage. The system may include any number of additional components that are positioned at an intermediate point in the system. Those intermediate components may be higher or lower than the acquisition point as long as the dispensing end is lower than the fluid surface at the acquisition point.

The siphoning effect drives flow through the system and is used to dispense the droplets. The siphoning allows for dispensing of individual intact sample droplets, and thus individual intact cells for culturing. Further description regarding systems driven by a siphoning effect is shown in Davies et al. (U.S. patent application Ser. No. 12/683,882, filed Jan. 7, 2010, and entitled "Sample Dispensing"), the contents of which are incorporated by references herein in their entirety.

In certain embodiments, the cells are cultured in the wrapped droplets. Media exchange may be accomplished by re-acquiring the droplets into the liquid bridge system using a sample acquisition device such as one described in McGuire et al. (U.S. patent application Ser. No. 12/468,367, filed May 19, 2009, and entitled "Sampling Device With Immiscible Fluid Supply Tube in Counter-Flow Arrangement," now U.S. Pat. No. 8,697,011), the content of which is incorporated by reference herein in its entirety.

Once the droplet has been acquired, the sample droplet is flowed to a liquid bridge where it is segmented, forming two droplets: a droplet of used culture media; and a droplet containing the cultured cells in a reduced volume of culture media. Droplet segmentation is described for example in Davies et al. (U.S. patent application number 2008/0277494), the content of which is incorporated by reference herein in its entirety.

After segmentation, the droplets are then flowed to a subsequent liquid bridge where a droplet of fresh cell culture media is introduced to the droplet containing the cell culture. In this manner, old culture media is removed from the cell culture and the cell culture is provided with fresh media. The droplet containing the cell culture is subsequently dispensed to a vessel for continued culturing or analysis and the droplet containing solely media is dispensed to waste. This process may be repeated as many times as necessary.

In other embodiments, the droplets may be dispensed to a vessel as wrapped droplets that are subsequently ruptured in the vessel. In certain embodiments, it is advantageous to ensure that a substantial portion of the carrier fluid is not dispensed into the collecting vessel. In one manner, flow rate is used to ensure that a substantial portion of the carrier fluid is not dispensed into the collecting vessel. The flow is controlled such that the dispensing port can be moved over a waste container to dispense the carrier fluid surrounding the droplets, and then moved over a collecting vessel to dispense the sample droplets. In this manner, a substantial a portion of the carrier fluid is not dispensed into the collecting vessel. Movement of the dispensing port is controlled by at least one robotics system.

Cells can be grown in suspension or adherent cultures. Some cells naturally live in suspension, without being attached to a surface, such as cells that exist in the bloodstream. There are also cell lines that have been modified to be able to survive in suspension cultures so that they can be grown to a higher density than adherent conditions would allow. Adherent cells require a surface, such as tissue culture plastic or microcarrier, which may be coated with extracellular matrix components to increase adhesion properties and provide other signals needed for growth and differentiation. Most cells derived from solid tissues are adherent. Depending on the type of cells to be cultured, the droplets may contain a support matrix or microcarrier. The liquid bridge may be used to introduce the microcarrier to the droplet containing the cells.

Once dispensed, the cells are cultured according to standard methods and protocols known to one of skill in the art. See for example, J. W. Pollard and J. M. Walker (Basic Cell Culture Protocols, 2nd ed.: Methods in Molecular Biology, Vol. 75, Humana Press, 1997); J. Davis (Basic Cell Culture: A Practical Approach, 2nd ed., Oxford University Press, 2002); S. Ozturk and W. Hu (Cell Culture Technology for Pharmaceutical and Cell-Based Therapies, CRC Press, 2005); A. Doyle and J. B. Griffiths (Cell and Tissue Culture for Medical Research, John Wiley & Sons, Ltd, 2000); A. Doyle, J. B. Griffiths (Cell and Tissue Culture: Laboratory Procedures in Biotechnology, John Wiley & Sons, Ltd, 1998); R. Ian Freshney (Culture of Animal Cells: A Manual of Basic Techniques, 5th ed., John Wiley & Sons, 2005); G. Vunjak-Novakovic and R. I. Freshney (Culture of Cells for Tissue Engineering, John Wiley & Sons, 2006); and R. Pfragner and R. Freshney (Culture of Human Tumor Cells, John Wiley & Sons, 2003). The contents of each of the above is incorporated by reference herein in its entirety.

Methods of the invention may be used with any cells. In certain embodiments, the cells are mammalian cells, such as human cells or animal cells. In other embodiments, the cells are cells from a human tissue or body fluid. A tissue is a mass of connected cells and/or extracellular matrix material, e.g. skin tissue, nasal passage tissue, CNS tissue, neural tissue, eye tissue, liver tissue, kidney tissue, placental tissue, mammary gland tissue, gastrointestinal tissue, musculoskeletal tissue, genitourinary tissue, bone marrow, and the like, derived from, for example, a human or other mammal and includes the connecting material and the liquid material in association with the cells and/or tissues. A body fluid is a liquid material derived from, for example, a human or other mammal. Such body fluids include, but are not limited to urine, sputum, stool, mucous, saliva, blood, plasma, serum, serum derivatives, bile, phlegm, sweat, amniotic fluid, mammary fluid, and cerebrospinal fluid (CSF), such as lumbar or ventricular CSF. The cell may also be from a fine needle aspirate or biopsied tissue. In particular embodiments, the cells are tumor cells. In other embodiments, the cells are brain cells or embryonic cells.

Another aspect of the invention provides methods for analyzing effect of at least one agent on a cell or cellular component. Methods of the invention involve forming a droplet wrapped in an immiscible carrier fluid, in which the droplet includes at least one cell or cellular component and at least one agent, and analyzing the wrapped droplet to determine effect of the agent on the cell or cellular component. Methods of the invention may be used to analyze effect of any agent, or combination of agents, on any cell or combination of cells. In certain embodiments, the cells are mammalian cells, such as human cells or animal cells. In other embodiments, the cells are cells from a human tissue or body fluid. In particular embodiments, the cells are tumor cells. The starting mixture of cells may be either homogeneous (i.e., a mixture including all the same type of cells) or heterogeneous (i.e., a mixture including a plurality of different types of cells).

In certain embodiments, methods of the invention are used to analyze specific cellular components, such as a nucleolus, a nucleus, a ribosome, a vesicle, a rough endoplasmic reticulum, a Golgi apparatus, cytoskeleton, a smooth endoplasmic reticulum, a mitochondria, a vacuole, a cytoplasm, a lysosome, or centrioles within centrosome. In particular embodiments, the cellular component is nucleic acid, such as DNA or RNA. Accordingly, cell may be lysed by using a liquid bridge to introduce a droplet containing a lysing agent to the droplet containing the cell. Formation of the mixed droplet mixes the lysing agent with the cell, lysing the cell and releasing the internal cellular components for subsequent analysis. The lysing agent may be a chemical agent, such as surfactants, solvents, or antibiotics.

Droplet generation may be accomplished as described above, and droplet generation may be controlled as described above to produce droplets that include only a single cell. Alternatively, droplets may be formed that include a plurality of cells.

The agent may be any agent or combination of agents. Exemplary agents are shown in The Merck Index (14th edition. Whitehouse Station, New Jersey, 2009), the contents of which are incorporated by reference herein in their entirety. In particular embodiments, the agent is an anti-cancer agent. Exemplary anti-cancer agents are shown in The Merck Index (14th edition. Whitehouse Station, New Jersey, 2009) and Dorr et al. (Cancer Chemotherapy Handbook, 2d edition, pages 15-34, Appleton & Lange, Connecticut, 1994), the contents of each of which are incorporated by reference herein in their entirety. In particular embodiments, the anti-cancer agent is altretamine, asparaginase, bleomycin, capecitabine, carboplatin, carmustine, cladribine, cisplatin, cyclophosphamide, cytarabine, dacarbazine, actinomycin D, docetaxel, doxorubicin, imatinib, etoposide, fludarabine, fluorouracil, gemcitabine, hydroxyurea, idarubicin, ifosfamide, irinotecan, methotrexate, mitomycin, mitotane, mitoxantrone, paclitaxel, topotecan, vinblastine, vincristine, vinorelbine, or combination thereof.

In certain embodiments, different concentrations of the same agent is provided to different cells, thus providing an ability to determine an effective dosage level or a toxicity level of an agent.

Any device that is capable of forming a sample droplets wrapped in an immiscible carrier fluid may be used with methods of the invention. An exemplary droplet device is a liquid bridge. Wrapped droplet formation using liquid bridges is described above. The sample droplets and the agent droplets may flow through a same channel, and flow may be used to cause the droplets to mix at the liquid bridge to form the mixed wrapped droplet. Alternatively, the sample droplets and the agent droplets may flow through different channels and meet for mixing at the liquid bridge.

After droplet mixing, the cell or cells in the mixed wrapped droplet are analyzed to determine the effect of the agent on the cell or cellular component in the droplet. Analyzing may be continuously, periodically or after a specific period of time. Analyzing involves monitoring characteristic analog outcome measures, which may include, but are not limited to: analog size, shape, density, color or opacity; changes in cell number; cell death or proliferation; changes in secreted materials such as cytokines, growth factors, hormones or extracellular matrix components; genetic markers that are up- or down-regulated during the culture period such as genes for receptors, cytokines, integrins, extracellular matrix molecules, or enzymes; and cell-surface molecules including integrins and receptors.

One method analyzing the cell or cells includes performing a cell viability and/or proliferative capacity assay. For example, Trypan blue is one of several stains recommended for use in dye exclusion procedures for viable cell counting. This method is based on the principle that Jive cells do not take up certain dyes, whereas dead cells do. Trypan blue is introduced to the cell or cells and the cells are observed for uptake of the stain. A hemocytometer may be used to observe the cell or cells. Methods for performing this assay are well known in the art.

Another method for analyzing the cell or cells includes RNA extraction and analysis by reverse transcriptase-polymerase chain reaction (RT-PCR). Cells in the construct are lysed and total RNA extracted with TRIZOL (Life Technologies, Rockville, Md.). Equal amounts (1 µg) of total RNA are subjected to reverse transcription into cDNA at 42° C. for one hour with oligo (dt$_{18}$) primers. The transcripts are then amplified by RT-PCR. Sample cDNA are also amplified for housekeeping genes such as rRNA subunit S14 for controls.

Another method for analyzing the cell or cells includes cytological-immunocytochemical analysis of cell products. Cells are fixed and stained with either hematoxylin-eosin (H&E) or with monospecific antibodies. Immunostaining for the marker or product of interest is visualized using immunoperoxidase technique with a substrate such as diaminobenzidine which will yield a brownish color. Cell preparations are counterstained with 0.5% toluidine blue.

Another method for analyzing the cell or cells includes western blots. Cells may be resuspended in lysis buffer containing protease inhibitors. Protein concentrations may be determined and total cell extracts may be electrophoresed on 7% SDS-polyacrylamide gel overlaid with stacking gel. The proteins are transferred from gel to nitrocellulose paper to immunolocalize the product using monospecific antibodies. To visualize the bands, the membrane blot may be exposed to BioMax Light Film (VWR, NJ).

Another method for analyzing the cell or cells includes determination of particular enzyme products. Enzymatic products may be assessed by serially diluting media samples and analyzing enzymatic activity using commercially available kits based on an enzyme linked immunoassay.

Other methods of analyzing the cells include ELISA assays, or microarray technology.

Analyzing of the cells may occur while the wrapped droplets are flowing through a channel. For example, for the cell viability assay, the mixed wrapped droplet may flow to a subsequent liquid bridge for an additional mixing step in which the mixed droplet mixes with a droplet of Trypan blue. The droplet now containing the cell(s), agent, and Trypan blue is flowed to a detection device (such as a CCD camera) that images the cells in the droplets as the droplets are flowing through the channel.

Alternatively, the droplets may be dispensed to a second vessel prior to analysis. Droplet dispensing may be accomplished as described above. Exemplary vessels include plates (e.g., 96 well or 384 well plates), eppendorf tubes, vials, beakers, flasks, centrifuge tubes, capillary tubes, cryogenic vials, bags, cups, or containers. In particular embodiments, the second vessel is a well plate and the droplets are dispensed into individual wells of the well plate, one droplet per well.

In certain embodiments, the droplet including the cell or cellular component is not mixed with an agent. Rather, the unmixed droplet is dispensed to at least one secondary vessel that already includes the agent. For example, droplets are dispensed to individual wells of a well plate in which each well of the plate already includes an agent or combination of agent. After dispensing, the cells are analyzed to assess the effect of the agent or combination of agents on the cell or cellular component.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A system for analyzing biological samples, the system comprising:
   a droplet generation subsystem comprising:
      a plurality of fluidic sources comprising a biological sample source, a lysing agent source, and a carrier fluid source, and
      a plurality of channels fluidically coupled to the biological sample source, the lysing agent source, and the carrier fluid source; and
   a flow control subsystem operably coupled to the plurality of channels, wherein the flow control subsystem is configured to control flow of the biological sample, the lysing agent, and the carrier fluid through the plurality of channels to form aqueous droplets of the biological sample and the lysing agent wrapped in the carrier fluid.

2. The system of claim 1, wherein the droplet generation subsystem further comprises a fluidic juncture coupled to the plurality of channels.

3. The system of claim 1, further comprising a droplet transfer subsystem configured to transfer the aqueous droplets from the droplet generation subsystem to a vessel.

4. The system of claim 3, wherein the droplet transfer subsystem is configured to control a pressure difference to drive a flow of the aqueous droplets from the droplet generation subsystem to the droplet transfer subsystem.

5. The system of claim 4, wherein the droplet transfer subsystem is configured to generate a negative pressure to transfer the aqueous droplets from the droplet generation subsystem.

6. The system of claim 3, further comprising the vessel, wherein the vessel is a multi-well plate, a tube, a vial, a beaker, a flask, a centrifuge tube, a capillary tube, a cryogenic vial, a bag, a cup, or a container.

7. The system of claim 1, further comprising an analysis subsystem configured to subject the aqueous droplets to an amplification reaction.

8. The system of claim 7, wherein the analysis subsystem is configured to perform a polymerase chain reaction (PCR) on the aqueous droplets.

9. The system of claim 7, wherein the analysis subsystem is configured to perform a reverse transcription-polymerase chain reaction (RT-PCR) assay on contents of the aqueous droplets.

10. The system of claim 7, wherein the analysis subsystem comprises a detection channel and a detection device configured to image cells in the aqueous droplets as the aqueous droplets flow through the detection channel.

11. The system of claim 1, wherein the flow control subsystem is configured to form a first subset of the aqueous droplets, each aqueous droplet of the first subset containing a single cell and the lysing agent.

12. The system of claim 1, wherein the droplet generation subsystem further comprises a source of microcarriers, wherein the flow control system is configured to flow the microcarrier and introduce a microcarrier into respective aqueous droplets.

* * * * *